United States Patent [19]

Forgione

[11] 3,949,065
[45] Apr. 6, 1976

[54] COMPOSITION AND METHOD FOR THE DETECTION OF SYPHILIS

[75] Inventor: Peter Salvatore Forgione, Stamford, Conn.

[73] Assignee: American Cyanamid Company, Stamford, Conn.

[22] Filed: Sept. 11, 1973

[21] Appl. No.: 396,168

[52] U.S. Cl............ 424/8; 23/253 TP; 210/DIG. 23; 424/11; 424/12; 424/13
[51] Int. Cl.² ................. G01N 21/04; G01N 31/02; G01N 33/16
[58] Field of Search............ 424/3, 11, 12, 13, 7, 8; 210/54, DIG. 23; 23/253 TP

[56] References Cited

UNITED STATES PATENTS

| | | | |
|---|---|---|---|
| 2,111,976 | 3/1938 | Laughlen | 424/8 |
| 2,112,496 | 3/1938 | Ide | 424/8 |
| 2,301,717 | 11/1942 | Terry | 424/8 |
| 2,770,572 | 11/1956 | Eldon | 424/11 |
| 3,074,853 | 1/1963 | Brewer | 424/12 |
| 3,406,114 | 10/1968 | Goren | 210/54 |
| 3,647,769 | 3/1972 | Bufton | 210/54 |
| 3,666,421 | 5/1972 | Price | 424/12 X |
| 3,695,999 | 10/1972 | Forgione | 195/63 |
| 3,737,037 | 6/1973 | Bone | 210/54 |

FOREIGN PATENTS OR APPLICATIONS

| | | | |
|---|---|---|---|
| 159,400 | 7/1972 | Hungary | 424/11 |

OTHER PUBLICATIONS

Benyo, Chem. Abs., Vol. 75, 1971 No. 61480b.
Berger, Chem. Abs., Vol. 38, 1944, p. 3996⁸.
Berger, British J. Exptl. Path. Vol. 24, 1943 pp. 252-260.
Chem. Abs., Vol. 68, 1968 No. 42944v.
Lillie, Histopath. Techic. & Pract. Histochem., McGraw-Hill Co., N.Y., 3rd Ed., 1965 pp. 114,119.

*Primary Examiner*—Sam Rosen
*Assistant Examiner*—A. P. Fagelson
*Attorney, Agent, or Firm*—Frank M. Van Riet

[57] ABSTRACT

An antigen preparation for use in the detection of syphilis and other treponemal diseases comprising (1) V.D.R.L. or U.S.R., antigen reagent and (2)

a. a compound having the formula

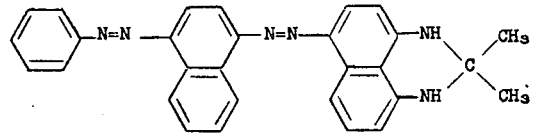

b. a compound having the formula

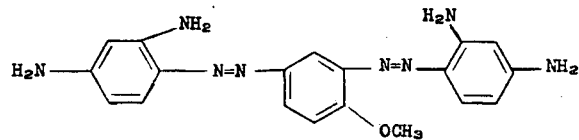

c. a compound having the formula

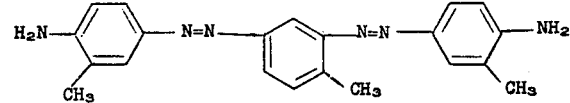

or (d) mixtures of (a) + (b) or (a) + (c), and (3) which may additionally include a polymeric flocculating agent. A method of using said antigen preparation and a test card having a flocculating agent deposited thereon, are also disclosed.

19 Claims, No Drawings

COMPOSITION AND METHOD FOR THE DETECTION OF SYPHILIS

BACKGROUND OF THE INVENTION

The use of serological tests for the detection of syphilis and other treponemal diseases has become more and more commonly practiced in recent years. These tests are usually based on an agglutination reaction and are conducted in clinics and doctors' offices preparatory to a more extensive diagnosis of the patient.

The most commonly practiced test constitutes the use of a finely divided solid such as charcoal in conjunction with a card having a surface color contrasting to that of the solid material, see U.S. Pat. No. 3,074,853. In practice, the test utilizes a common antigen liquid which is buffered and to which is added the charcoal. A drop of the resultant antigen solution-charcoal suspension is then placed on a test card in admixture with one drop of serum. The card is then shaken and the results are visually interpreted. A further syphilis testing method has been reported by Lockyer, *Brit. Journal Vener. Dis.*, Vol. 46, pages 290–294, 1970. This test entails the use of a scarlet red powder coupled with a Kahn antigen. Additional diagnostic reagents have recently been patented, see U.S. Pat. Nos. 3,564,089 and 3,600,494.

The known test methods, while resulting in adequate syphilis detection in most cases, are by no means perfect and each possesses its own difficulties. The charcoal test, for example, is very difficult to interpret due to the tendency of the positive and negative results to be similar in many instances. Where a definitely positive test is encountered, no difficulty arises, however, in cases where the results are in doubt, further, more extensive tests must be conducted before a definite conclusion can be drawn. The Lockyer test results in the production of a pink flocculated material but this material is very difficult to detect since the particles are very minute. Being pink, the color is not as easily detected as with the charcoal test or that of my novel invention. It has additionally been well recognized that other commonly used tests have been known to give completely erroneous results in 2.0% of the tests run and false positive results in 20% of the test cases.

SUMMARY OF THE INVENTION

I have now found a novel visual method for the detection of syphilis and other treponemal diseases which has material advantages over other techniques such as the use of charcoal, very lightly colored systems or latex emulsions. Since my system does not utilize solid particles, no light scattering is caused and therefore a more easily visible particle is produced if a positive serum is used and being dark colored, the visibility is even more pronounced. Therefore, the instant test is more accurate and reliable.

According to my novel test, when my novel antigen reagent is contacted with a serum containing antibody, a complex is formed which forms a coaccervate with the components of the antigen test reagent. A positive test is indicated by darkly colored flocs on a light background, i.e. a white card.

DESCRIPTION OF THE INVENTION INCLUDING PREFERRED EMBODIMENTS

As mentioned briefly above, I have discovered a novel antigen preparation for use in carrying out an agglutination test for syphilis and other treponemal diseases. The antigen preparation consists of two basic ingredients, the first being a common V.D.R.L. or U.S.R. antigen reagent known to those skilled in the art and more completely identified in U.S. Pat. No. 3,564,089, mentioned above.

The second component of my novel antigen preparation is a dye compound having the formula (I)

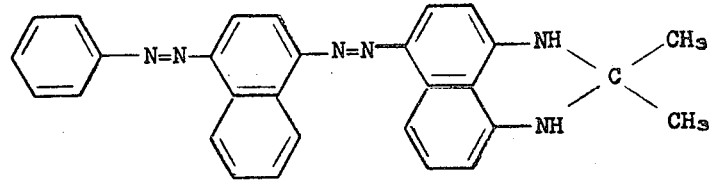

(II)

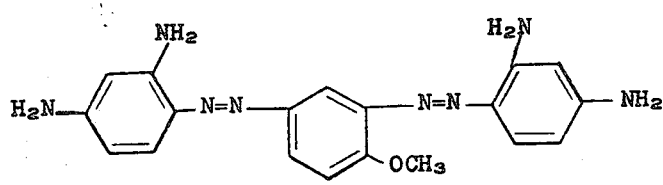

(III)

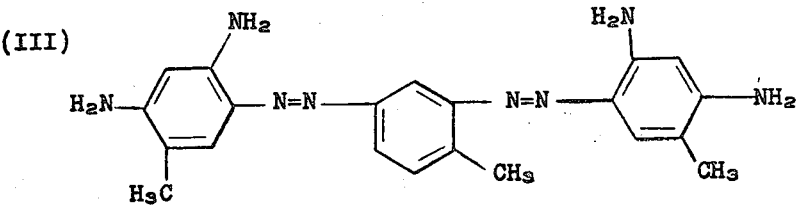

or mixtures of (I) + (II) and (I) + (III).

The dye compounds and mixtures are present in my novel antigen preparations in conjunction with solvents, buffers etc. in a manner as is known in the art. These solvents, buffers etc. per se form no part of the instant invention and are used as described in known antigen systems such as those discussed in the above-identified U.S. Patents, hereby incorporated herein by reference.

The components of the novel antigen preparation of my invention are employed in concentrations ranging from about 0.5% to about 25.0%, by weight, of the standard V.D.R.L. or U.S.R. antigen and from about 0.0001% to about 0.2%, by weight, of the dye compounds, said weights being based on the total weight of the resultant mixture including solvents e.g. water, alcohol etc. and buffer.

When the mixtures of the dye compounds of Formulae I, II and III above, are employed, the total amount of mixture should fall within the above specified range for the dye compound but the ratio of one compound to the other can range from about 9:1 to about 1:9, respectively.

By "standard V.D.R.L. and U.S.R. antigen", as used herein, is meant the compositions set forth and prescribed by the Manual of Tests for Syphilis (1969), U.S. Dept. of Health, Education and Welfare, Public Health Service, National Communicable Disease Center.

A third component may also be present in my novel antigen preparations. This component is preferred but not critical and comprises a flocculating agent. The flocculating agent can be employed in amounts ranging from about 0.0001% to about 0.05%, by weight, based on the total weight of the novel antigen preparation of the instant invention i.e. standard antigen and dye, compound, and includes such known flocculants as vinylimidazoline, acrylamide, acrylic acid, acrylonitrile, styrene, maleic anhydride, etc. polymers and copolymers thereof with each other and other known copolymerizable monomers.

In practice, the flocculating agent aids in the precipitation and coaccervation of the antigen-antibody complex and thereby aids in the visual detection of the positive test.

In preparing the antigen formulations of the present invention, standard V.D.R.L. antigen can be used. The dye compound or compounds may be incorporated into an alcoholic solution of the V.D.R.L. antigen or added after the reagent antigen has been prepared in buffer. If a flocculating agent is to be incorporated into the basic preparation, it is also added with slight agitation at this time.

The U.S.R. antigen-dye compound formulation is made by first preparing the V.D.R.L. antigen suspension in buffer. This system is then centrifuged in a stainless steel vessel at approximately 2,000 g for 15 minutes. The fluid is decanted and the sides of the vessel wiped dry. The sediment is suspended in U.S.R. suspending medium which consists of a known and appropriate mixture of monopotassium phosphate, disodium phosphate, merthiolate, choline chloride and ethylenedinitrilotetraacetic acid. The dye compound or compounds may be incorporated into the alcoholic solution of V.D.R.L. antigen or the U.S.R. antigen after its suspension in U.S.R. suspending medium.

The instant invention also encompasses a test card having a flocculating agent deposited thereon. The test card should be smooth in order to render the test results easily discernible. Although it has been previously indicated in the prior art that the surface must be wettable, I have found that such is not the case and a wettable surface is merely preferred. The card may be composed of well calendered paper or cardboard and may be absorbable, however, only small degrees of absorbability are preferred. One feature of my test, however, is that the test may be read whether the spot is wet or dry and therefore results can be ascertained more rapidly than when using other techniques. The card may also be a laminate of a paper or cardboard base having a water-permeable or water-impermeable material coated thereon such as polyethylene. The paper itself or the coating, however, should be of a color which is contrasting with regard to the color of the dye or dyes employed in the test. Basically, my card is similar in construction and composition to that disclosed in U.S. Pat. No. 3,074,853. The flocculating agent may be deposited on the card by merely evaporating it from a solution after having placed a solution thereof thereon. The solvent may be either water or an organic material such as methylene chloride etc. Although the flocculating agent tends to adhere to the card sufficiently to provide excellent results, an adhesive may also be added to the card beforehand to insure adequate adhesion. A suitable adhesive for this purpose is methyl cellulose. The same flocculating agents as mentioned above with regard to direct addition thereof to the flocculating agent is usually deposited in selected areas only of the test card, these areas usually being designated as a circle etc., the area at which the test is actually conducted. When the flocculating agent is present on the card per se, it is not necessary to add further flocculating agent to the antigen preparation being used to conduct the test.

Tests are usually carried out by shaking the cards after the antigen preparation and serum have been added dropwise thereto. The shaking may be carried out on, for example, a horizontal disc about 10 inches square at about 80–240 strokes per minute with a slight eccentric motion. However, hand shaking is also effective.

The following examples are set forth for purposes of illustration only and are not to be construed as limitations on the instant invention except as set forth in the appended claims. All parts and percentages are by weight unless otherwise indicated.

EXAMPLE 1

U.S.R. Test

The antigen used in this test is an alcoholic solution of 0.03% cardiolipin, 0.9% cholesterol and 0.21 ± 0.01% lecithin. This standard V.D.R.L. antigen and the standard buffered saline diluent for the preparation of the reagent V.D.R.L. antigen are commercially available.

Unheated Serum Reagin (U.S.R.) Test

Preparation of U.S.R. Antigen-Dye Compound Reagent

A. EDTA (0.1 M)
   Dissolve 3.72 g [(ethylenedinitrilo)tetraacetic acid disodium salt](EDTA) to a volume of 100 ml.
B. Choline Chloride Solution (40%)
   Dissolve the contents of a 250 g bottle of choline chloride in distilled water to a final volume of of 625 ml. Filter and store at room temperature.
C. Phosphate (0.02 M), Merthiolate (0.2%) Solution
   Dissolve 1.42 g $Na_2HPO_4$, 1.36 g $KH_2PO_4$, 1.00 g merthiolate in distilled water to a final volume of 500 ml. at a pH of 6.9.

| Suspending Solution | |
|---|---|
| Solution A | - 1 part |
| Solution B | - 2 parts |
| Solution C | - 4 parts |
| Distilled Water | - 1 part |

Preparation of the Antigen Suspension 1.6 Ml of commercially available V.D.R.L. buffered saline are pipetted to the bottom of a 30 ml flat-bottom, glass-stoppered vessel. Two (2.0) ml of antigen is added drop by drop so that it is added in about six seconds directly onto the saline solution. The vessel is then continuously but gently rotated on a flat surface while the antigen is being added. The last drop is blown out without touching the pipette to the saline solution. The vessel is rotated for an additional 10 seconds. Sixteen and four tenths (16.4) ml of standard buffered saline is then added and the vessel shaken (with the top on) bottom to top and back thirty (30) times in about 10 seconds. The resultant product is the V.D.R.L. antigen suspension used below.

The above prepared V.D.R.L. antigen suspension is centrifuged in an angle centrifuge at room temperature at a relative centrifugal force of approximately 2,000 x g for 15 minutes. The supernatant fluid is decanted by inverting the tube away from the side containing the sediment. The inside of the vessel is wiped with a cotton gauze without disturbing the sediment while the tube is held in an inverted position. The sediment is then resuspended in the above suspending solution with a volume equal to that of the original portion of antigen suspension that was centrifuged. If more than one container is used for centrifuging, the contents are pooled and mixed gently. The result is U.S.R. antigen. Seven hundredths (0.07) ml of a 1% solution of "Sudan Black", having the formula I, above, and identified as Sudan Black-C.I. No. 26150, is slowly added to the U.S.R. antigen while the antigen is gently agitated. The result is an antigen preparation ready for testing.

Procedure for the Detection of Reagin Antibody
(U.S.R. Test)

The test may be conducted on serum or plasma samples which have not been heated, although heat inactivated samples are satisfactory.

Fifty (50) $\mu$l of serum and 1/60 ml of the above antigen preparation are added to a commercially available white test card. The mixture is briefly mixed with a mixing stick or other device. The card is then put on a clinical rotator and rotated for 6 minutes at 130 r.p.m. Black aggregated antigen-dye particles are visible under an incandescent, incident beam of light, denoting a positive syphilis test. A negative reaction is one in which the reagents do not aggregate into discrete particles but remain as a homogenous suspension.

EXAMPLE 2

Antigen Preparation

To the V.D.R.L. antigen suspension (see above) is added 0.04 ml of 0.1% alcoholic solutions of Basic Brown and Sudan Black (1:1 ratio) having the formulae II and I, above, and designated as Basic Brown-C.I. No. 21030 and Sudan Black C.I. No. 26150, respectively. The antigen preparation is now ready for use.

Procedure for the Detection of Reagin Antibody
(V.D.R.L. Test)

Plasma is removed from the blood cells of a suspect patient and heated at 56°C. for 30 minutes. Fifty (50) $\mu$l of the sample and 1/60 ml of the above V.D.R.L. antigen preparation are placed on a commercially available white test card. After mixing, the card is placed on a clinical rotator and rotated as in Example 1. Aggregated black particles visible under an incandescent, incident beam of light denote a positive syphilis test. A negative reaction is one in which the reagents do not aggregate into discrete particles but remain as a homogenous dispersion.

EXAMPLE 3

An antigen preparation is again produced as in Example 1. The test is conducted in the same manner as the U.S.R. test except that one (1) $\mu$l of a 0.1% aqueous solution of polyvinylimidazoline is added to the test card and dried at room temperature before rotating. The aggregated particles are such that visibility thereof is further enhanced over the card wherein no imidazoline polymer is used.

EXAMPLE 4

An antigen preparation is produced as in Example 2. The test is conducted in the same manner as the V.D.R.L. test except one (1) $\mu$l of a 0.1% aqueous solution of polyvinylimidazoline is added to the test card and dried as in Example 3. Visibility of the aggregated particles is again amplified.

EXAMPLE 5

The procedure of Example 2 is again followed except that the Basic Brown-C.I. No. 21030 is eliminated. Again clearly visible, but less dark, aggregated particles are recorded indicative of a positive syphilis reaction.

EXAMPLE 6

The procedure of Example 1 is again followed except that the dye mixture of Example 2 is added to the U.S.R. antigen rather than the single dye compound alone. A positive syphilis reaction is indicated by dark aggregated particles.

EXAMPLE 7

Addition of a commercially available polyacrylate flocculating agent (0.0015%) as a 0.1% aqueous solution, to the test card used in Example 5, before addition of the antigen preparation, results in the formation of larger aggregated particles of dark color, increasing the ease of reading and therefore the accuracy of the test. Positive results are indicated.

EXAMPLE 8

A commercially available flocculating agent based on an acrylamide polymer as added to a white syphilis test card and dried at room temperature. The procedure of Example 6 is again carried out utilizing the resultant card. Large, dark aggregated particles are observed, the size of the particles being somewhat larger than those of Example 6.

EXAMPLE 9

The procedure of Example 1 is again followed except Basic Brown-C.I. No. 21010, having formula III, above, is used in place of the dye compound used therein. Similar results are achieved.

EXAMPLE 10

In place of the dye compound of Example 2, is added an equivalent amount of Basic Brown-C.I. No. 21010, (Formula III). Again dark, aggregated particles are observed indicating a positive syphilis result.

EXAMPLE 11

The procedure of Example 2 is again followed except that an equivalent amount of a mixture (ratio 9:1) of Sudan Black-C.I. No. 26150 and Basic Brown-C.I. No. 21010 is used. A positive reaction is observed in the form of large, aggregated black particles.

EXAMPLE 12

The dye compound mixture of Example 11 is utilized in Example 1 in lieu of the single dye compound used therein. A positive result is easily ascertained.

EXAMPLE 13

Basic Brown-C.I. No. 21030, shown as Formula II, above, is used in place of the Sudan Black of Example 1. Similar results are achieved except that the particles are brown instead of black.

EXAMPLE 14

The procedure of Example 2 is again followed except that double the amount of Basic Brown-C.I. No. 21030 is used and Sudan Black-C.I. No. 26150, is omitted. Again the skilled clinician can readily observe the resultant positive reaction indicated by the brownish, aggregated particles.

EXAMPLES 15–18

The test card produced in Example 7 is used to conduct the tests of Examples 11, 12, 13 and 14. The flocculating agent present on the test cards, in each instance, enhances the size of the aggregated particles and even further adds to the ease of analysis by the clinician. All cards show a positive result.

EXAMPLE 19

To a commercially available, white syphilis test card is added 1.5% of a 0.1% aqueous solution of a styrene-maleic anhydride flocculating agent. The card is allowed to dry at room temperature. When used in a syphilis test in a known manner, the aggregated particles indicating a positive reaction are larger and more easily discernible than when the flocculating agent is omitted from the card.

I claim:
1. An antigen preparation for use in carrying out an agglutination test for syphilis which consists essentially of
  I. from about 0.5 to about 25.0%, by weight, based on the total weight of said preparation, of a syphilis antigen reagent,
  II. from about 0.0001 to about 0.2%, by weight, same basis, of a dye compound having the formula

(a) 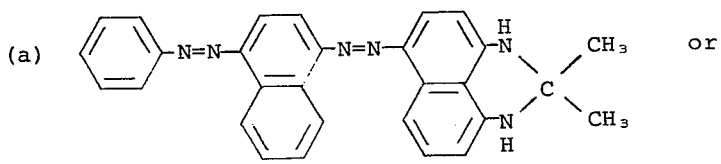 or (b) 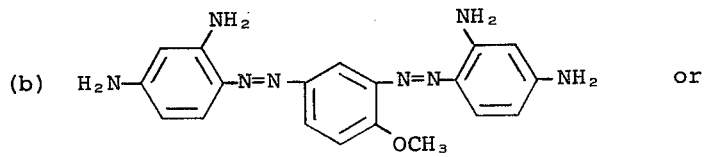 or (c) 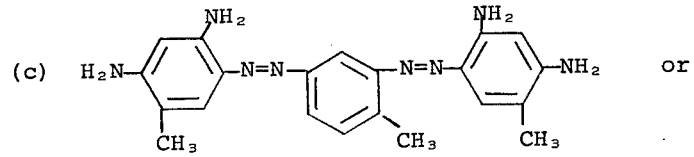 or d. mixtures of (a) and (b) or (a) and (c) and
  III. from about 0.0001% to about 0.05%, by weight, same basis, of a polymeric flocculating agent selected from the group consisting of polyvinylimidazoline, a polyacrylate, an acrylamide polymer and a styrene-maleic anhydride copolymer, the remainder of said preparation being solvent and buffer.

2. The antigen preparation of claim 1 wherein said dye compound has the formula

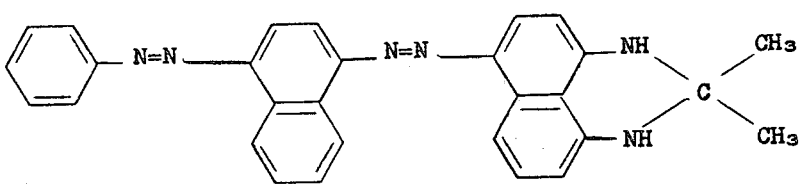

3. The antigen preparation of claim 1 wherein said dye compound has the formula

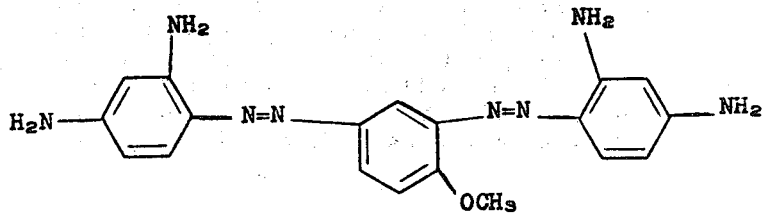

4. The antigen preparation of claim 1 wherein said dye is a mixture of (a) and (b).

5. The antigen preparation of claim 1 wherein said dye compound has the formula

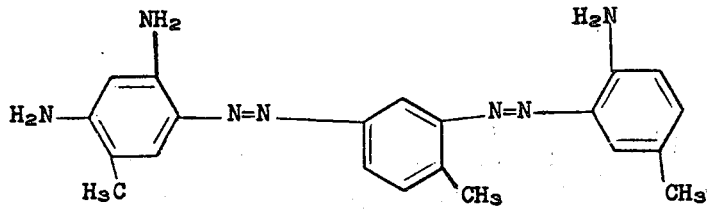

6. The antigen preparation of claim 1 wherein said dye is a mixture of (a) and (c).

7. A method for carrying out an agglutination test for syphilis which comprises contacting (1) a test serum or plasma with (2) the antigen preparation of claim 1.

8. The method of claim 7 wherein said dye compound has the formula

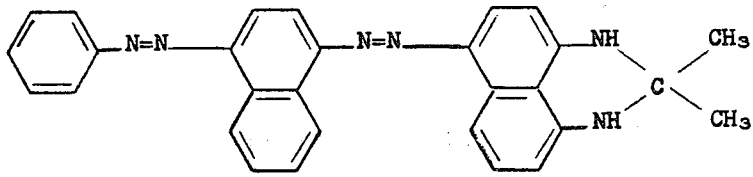

9. The method of claim 7 wherein said dye has the formula

[structure of compound]

10. The method of claim 7 wherein said dye is a mixture of (a) and (b).

11. The method of claim 7 wherein said dye compound has the formula

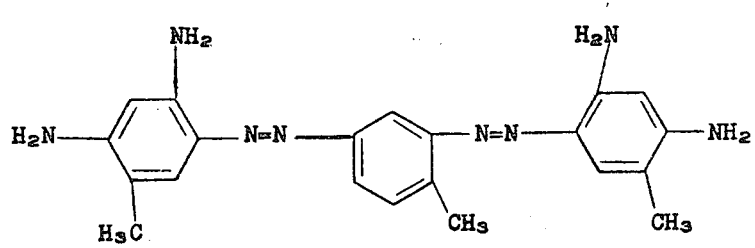

12. The method of claim 7 wherein said dye is a mixture of (a) and (c).

13. An antigen preparation for use in carrying out an agglutination test for syphilis which consists essentially of,
I. from about 0.5 to about 25.0%, by weight, based on the total weight of the preparation, of a syphilis antigen reagent, and
II. from about 0.0001 to about 0.2%, by weight, same basis, of a dye comprising:
a. a mixture of

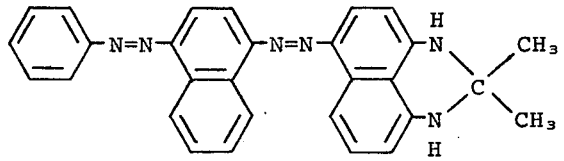

and

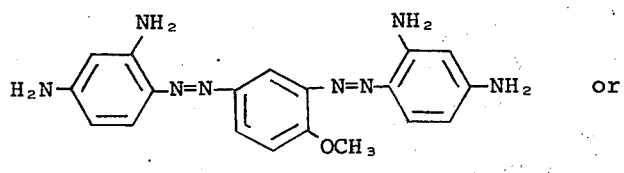

or (b) a mixture of

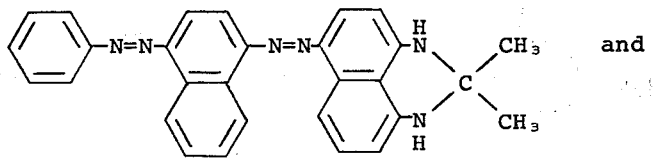

and

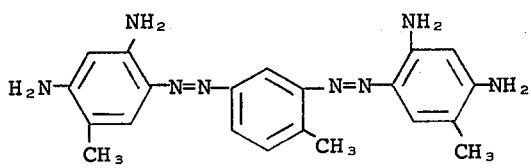

the ratio of the components of said mixtures ranging from about 9 : 1 to about 1 : 9, respectively, the remainder of said preparation being solvent and buffer.

14. The antigen preparation of claim 13 wherein said dye comprises mixture (a).

15. The antigen preparation of claim 13 wherein said dye comprises mixture (b).

16. A method for carrying out an agglutination test for syphilis which comprises mixing (1) a test serum or plasma, and (2) the antigen preparation of claim 13 with (3) a dried test spot comprising a polymeric flocculating agent on a solid sheet having a smooth surface.

17. A method for carrying out an agglutination test for syphilis which comprises contacting (1) a test serum or plasma with (2) the antigen preparation of claim 13.

18. The method of claim 17 wherein said dye comprises mixture (a).

19. The method of claim 17 wherein said dye comprises mixture (b).

* * * * *